(12) United States Patent
Bleau (10) Patent No.: US 7,188,946 B2
(45) Date of Patent: Mar. 13, 2007

(54) EYEWEAR

(75) Inventor: Michael James Bleau, Grand Blanc, MI (US)

(73) Assignee: SharkLids EyeGear, LLC, Grand Blanc, MI (US)

( * ) Notice: Subject to any disclaimer, the term of this patent is extended or adjusted under 35 U.S.C. 154(b) by 0 days.

(21) Appl. No.: 11/230,313

(22) Filed: Sep. 19, 2005

(65) Prior Publication Data

US 2006/0070161 A1    Apr. 6, 2006

Related U.S. Application Data

(63) Continuation of application No. 10/205,238, filed on Jul. 25, 2002, now Pat. No. 6,984,037.

(51) Int. Cl.
*G02C 11/08* (2006.01)

(52) U.S. Cl. .................... 351/62; 351/41; 351/154

(58) Field of Classification Search ............... 351/41, 351/44, 62, 83, 86, 154
See application file for complete search history.

(56) References Cited

U.S. PATENT DOCUMENTS

| | | | |
|---|---|---|---|
| 583,590 A | 6/1897 | Bennett | 2/447 |
| 2,149,514 A | 3/1939 | Fischer | 2/436 |
| 2,243,982 A | 6/1941 | Seeley | 2/12 |
| 2,387,851 A | 10/1945 | Lonn et al. | 2/441 |
| 2,430,881 A | 11/1947 | Lehmberg | 2/437 |
| 3,092,103 A | 11/1959 | Mower | 128/858 |
| 3,614,216 A | 10/1971 | Rosenthal | 351/44 |
| 3,701,592 A | 10/1971 | Fernandez | 351/130 |
| 4,006,974 A | 2/1977 | Resnick | 351/59 |
| 4,122,847 A | 10/1978 | Craig | 128/858 |
| 4,393,080 A | 7/1983 | Pawelchak et al. | 428/355 R |
| 4,547,909 A | 10/1985 | Bell | 2/431 |
| 4,797,956 A | 1/1989 | Boyce | 2/12 |
| 4,837,862 A | 6/1989 | Heil | 351/111 |
| 4,886,349 A | 12/1989 | Willis | 351/111 |
| 4,944,294 A | 7/1990 | Borek, Jr. | 128/206.19 |
| 5,016,999 A | 5/1991 | Williams | 351/41 |
| 5,020,533 A | 6/1991 | Hubbard et al. | 128/206.23 |
| 5,302,977 A | 4/1994 | Markovitz et al. | 351/114 |
| 5,383,450 A | 1/1995 | Hubbard et al. | 128/206.23 |
| 5,406,944 A | 4/1995 | Gazzara | 128/206.19 |
| 5,419,913 A | 5/1995 | Podell et al. | 424/448 |
| 5,425,380 A | 6/1995 | Hudson et al. | 128/858 |
| 5,584,078 A | 12/1996 | Saboory | 351/111 |
| 5,700,238 A | 12/1997 | Hyson | 2/427 |

(Continued)

FOREIGN PATENT DOCUMENTS

JP    11 128378    5/1999

(Continued)

*Primary Examiner*—Huy Mai
(74) *Attorney, Agent, or Firm*—Goodwin Procter LLP (57) ABSTRACT

Novel eyewear are disclosed which comprise a lens and a sealing frame. The lens is adapted to cover at least one of a user's eyes. The frame has an adhesive side and is disposed adjacent the perimeter of the lens. A first portion of the adhesive side is disposed at the perimeter of the lens forming a seal between the frame and the lens. A second portion of the adhesive side extends laterally beyond the perimeter of said lens to provide adhesive attachment of the eyewear to the face of the user.

18 Claims, 7 Drawing Sheets

U.S. PATENT DOCUMENTS

| | | | |
|---|---|---|---|
| 5,719,655 A | 2/1998 | Peschel et al. | 602/74 |
| 5,797,146 A | 8/1998 | Matich | 2/424 |
| 5,949,514 A | 9/1999 | Wargon | 351/41 |
| 6,019,103 A | 2/2000 | Carroll | 128/858 |
| 6,026,511 A | 2/2000 | Baumann et al. | 2/9 |
| 6,196,223 B1 | 3/2001 | Belfer et al. | 128/206.19 |
| 6,216,695 B1 | 4/2001 | Ruben | 128/206.14 |
| 6,526,975 B1 | 3/2003 | Chung | 128/206.19 |
| 6,543,450 B1 | 4/2003 | Flynn | 128/206.25 |
| 6,609,516 B2 | 8/2003 | Hollander et al. | 128/201.17 |
| 6,761,447 B1 | 7/2004 | Pyo | 351/41 |
| 6,776,485 B2 | 8/2004 | Cole | 351/158 |
| 6,984,037 B2 * | 1/2006 | Bleau | 351/83 |

FOREIGN PATENT DOCUMENTS

| | | |
|---|---|---|
| WO | WO 97/21397 | 6/1997 |
| WO | WO 02/06881 | 1/2002 |

* cited by examiner

EYEWEAR

This is a continuation of prior application Ser. No. 10/205,238, filed on Jul. 25, 2002, now U.S. Pat. No. 6,984,037, the entire disclosure of which is incorporated by reference herein.

FIELD OF THE INVENTION

The invention relates to eyewear, specifically to goggles and eye shields, that provide protection and/or vision enhancement, particularly where a closely conforming, flexible material contacts the area surrounding the eye for the purpose of sealing a lens or shield against the wearer's face for activities such as swimming. The eyewear can also be used in medical applications for protection against exposure to body fluids, or in recreational applications such as sunglasses.

BACKGROUND OF THE INVENTION

Goggles are commonly used to keep a user's eyes isolated from the surrounding atmosphere. For example, swimming goggles are utilized to protect the eyes from water. Other goggles, such as protective goggles, prevent exposure of the user's eyes to toxins or contaminated material, such as blood or eye irritants. Goggles may also be used to protect the eyes from harmful or undesirable environmental conditions, such as cold or dry air or sand or dust in the air. Goggles may also be used to retain a particular fluid or gas in contact with the user's eyes or face.

Generally speaking, eye goggle designs employ soft, spongy material between the area surrounding a user's eyes and the perimeter of the goggle lens and a head strap to hold the goggles in place against the wearer's face. For example, traditional swimming goggles seal each eyepiece or lens against the face in a water tight manner by the elastic force of a head strap pulling the eyepiece against the face, and suction forces created during the fitting of the goggles onto the user's face, leaving negative pressure inside the eyepiece.

It is well known in the art that these forces create pressure points and a certain amount of discomfort in exchange for a water-tight fit. Greater forces generally impart greater discomfort, but also a more secure fit against leakage.

Traditional, strap-type swimming goggles can slip off of the wearer's face during diving or flip-turns where the wearer is moving at higher velocity through the water than when simply swimming. It would be desirable to have goggles that provide a more secure fit and a low profile to reduce drag and that will remain in place on the user's face. In medical applications, the wearer being an EMT, surgeon or other type of health care provider, would benefit from a disposable, inexpensive eye shield that not only protects the wearer from fluid exposure, but also the patient from possible contamination of sweat dripping from the health care worker onto or into the patient.

Thus, it is desirable to develop a goggle design that provides a substantially water-tight seal for a user's eyes that eliminates or reduces the need for straps or elastic bands or requirements for additional forces to retain the goggles in place over the user's eyes.

It is also desirable to develop a face or eye shield design that provides isolation of a user's eyes or face that eliminates or reduces the need for straps or elastic bands or the requirement for additional forces to retain the face or eye shield in place over the user's face or eyes.

SUMMARY OF THE INVENTION

An object of this invention is to provide an economical yet precisely made, preferably optically clear eyewear such as goggles which extends broadly the range of comfortable fit for a user requiring closely conforming eye protection.

The present invention provides eyewear for protection of a user's eyes and isolation thereof from the outside environment. The eyewear generally comprises two components, namely a lens and a sealing frame. The lens is adapted to cover at least one of a user's eyes. The sealing frame has an adhesive side, which is disposed along the perimeter of said lens. A first portion of the sealing frame adhesive side is disposed at the perimeter of said lens forming a substantially airtight or watertight seal between said frame and said lens. A second portion of sealing frame adhesive side extends from said first portion laterally beyond the perimeter of said lens. The second portion provides a means for forming a substantially airtight or watertight seal between the sealing frame and at least a portion of the user's face adjacent the perimeter of said lens.

In a preferred embodiment, the interior side of the lens has a fog resistant coating. In another preferred embodiment, the lens has UV protection incorporated therein or thereon. The exterior side of the lens may optionally have a water-shedding coating.

DETAILED DESCRIPTION OF A PREFERRED EMBODIMENT

Figure 1:
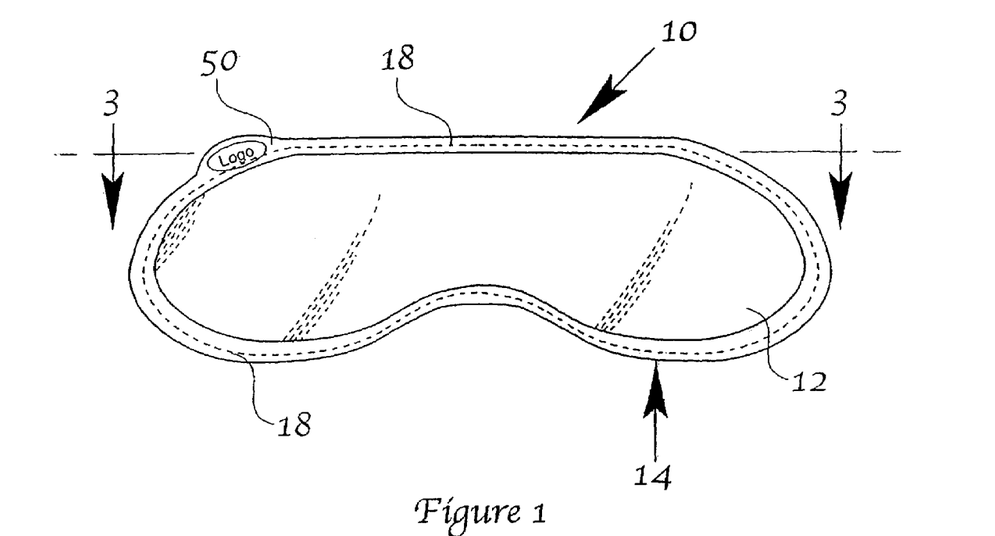
FIG. 1 is a top plan view of eyewear according to the present invention.
Figure 2:
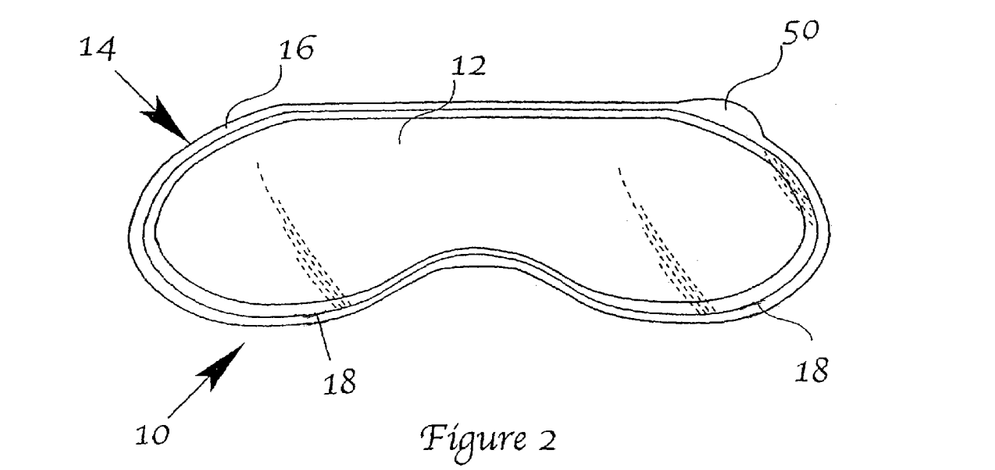
FIG. 2 is a bottom plan view of eyewear according to the present invention.

FIGS. 1 and 2 show eyewear 10 in accordance with the present invention. Eyewear 10 generally provides protection to the eyes of a user during use by isolating the user's eyes from the outside environment. In an alternative embodiment, this eyewear can be used to retain a particular fluid or gas in contact with the user's eyes or face.

The eyewear 10 generally comprises two components, namely a lens 12 and a frame 14. The lens 12 is adapted to cover at least one of a user's eyes. At least a portion, and preferably the entire lens 12 is transparent. In an alternative embodiment, however, the lens is opaque, thereby preventing all visible light from passing through the lens to the user's eyes. The lens material may be flexible, semi-rigid or rigid in nature. If the lens material is semi-rigid or rigid, the contour of the lens should generally conform to the shape and contours of the user's face. This is particularly desirable around the user's eyes to accommodate the user's eyes behind the lens and away from the environment from which protection is desirable. The lens material, however, is flexible in nature, thereby allowing the lens 12 to conform to the shape and contours of a user's face around the user's eyes. This provides for greater freedom from a manufacturing perspective to the extent that a uniform lens can be manufactured from a flexible material for a segment of user's, thereby averting the need to customize the lens for each user since the lens will conform to the contours of user's face during application of the eyewear onto the user's face.

Suitable materials for the lens include polyvinyl chloride (PVC), acrylics, polyester film, such as Mylar (commercially available from Dupont), and polystyrene including general-purpose polystyrene and high impact polystyrene. The lens material can be virtually any type of material that can be designed to fit and generally conform to the shape of the user's face and around the user's eye socket. The lens material is preferably a transparent, plastic material. In one embodiment, the material is a thin film of transparent, flexible plastic material that is sized such that the perimeter of the lens runs along the contours of the user's face beyond the user's eye sockets to fit outside the user's orbit.

In a preferred embodiment of the invention, lens material comprises a clear plastic material such as 2 mil thick polystyrene. The lens material may be coated to resist fogging as well as protect against UV penetration. Also, the exterior of the lens preferably has a water-shedding coating, which is particularly useful in an embodiment for use as a swim goggle.

The frame 14 of the eyewear 10 has an adhesive side 16, which is disposed adjacent or runs generally along the perimeter 18 of the lens 12. A first portion of the frame adhesive side is disposed at the perimeter of said lens forming a substantially airtight or watertight seal between said frame and said lens. A second portion of sealing frame adhesive side extends from said first portion laterally beyond the perimeter of said lens. The second portion provides a means for forming a substantially airtight or watertight seal between the sealing frame and at least a portion of the user's face adjacent the perimeter of said lens.

Suitable material for the frame 14 is a flexible, compliant, preferably elastic material that will conform to the contours of the user's face. The frame material will have an adhesive characteristic on at least the portion defining the adhesive side 16. Thus, the frame may comprise flexible, compliant adhesive material which possesses the desirable adhesive properties or may comprise flexible, compliant material to which has been applied an adhesive substance providing the adhesive properties. Such materials are well known in the art.

In a preferred embodiment of the invention, the frame material comprises a hypoallergenic material such as 3M Corporation's Medical Specialties Health care division's product number 1526, being a 3.6 mil thick, transparent, polyethylene film, coated on one side with a hypoallergenic pressure sensitive acrylate adhesive. The tape is supplied on a polyethylene-coated, bleached Kraft paper liner, with a basis weight of 63 pounds, silicone coated one side, which has a nominal caliper of 4.9 mil. According to 3M product clinical data summaries for safety testing, the 1526 material has been subjected to the safety tests that provide adequate hypoallergenic properties.

Figure 3:
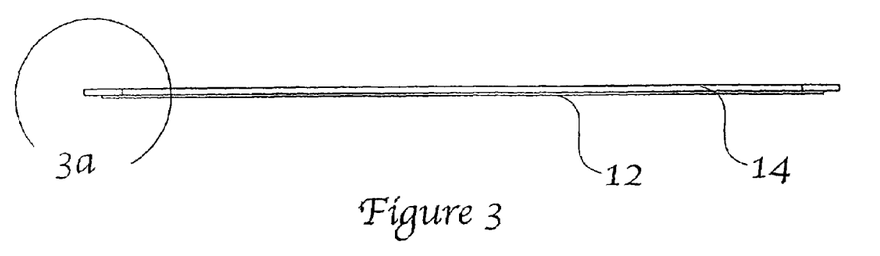
FIG. 3 is a cross-sectional view of eyewear according to the present invention along line 3—3 of FIG. 1.
Figure 3A:
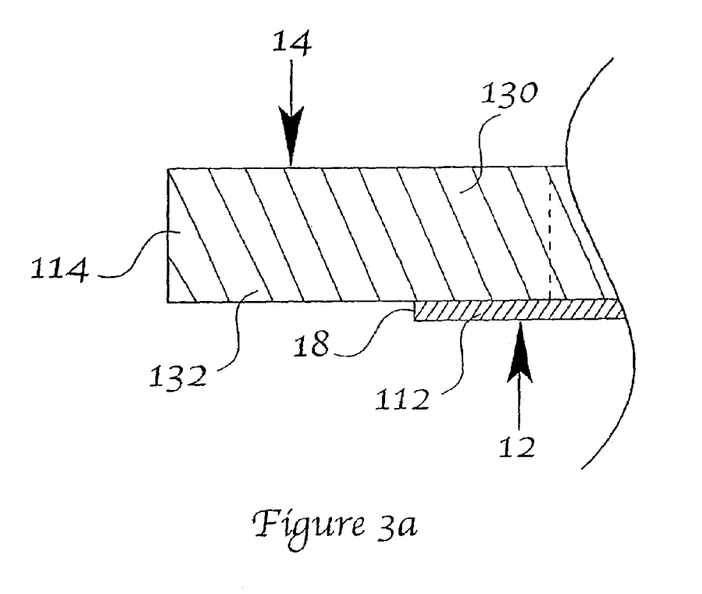
FIG. 3a is a partial, magnified cross section of an end of the eyewear 3a in FIG. 3.

In FIGS. 3 and 3a, frame 14 is shown disposed adjacent lens 12 and adhesively attached thereto particularly along perimeter 18 of lens 12. As seen in FIG. 3a, frame end 114 overlays lens end 112 such that the frame end 114 extends beyond perimeter 18 of lens 12. As described previously, frame 14 has an adhesive side that provides assembly of the eyewear 10 along a first portion 130 of frame 14. Further, the adhesive side 16 of frame 14 provides a means of adhesive attachment to the face of a user, preferably in a releasable manner, along a second portion 132 of frame 14. Although the construction of the eyewear is illustrated herein as provided by adhesive attachment between the frame and lens, any means of attachment between the frame and lens in the first portion of the frame that is known in the art can be utilized for such construction. This would include laser bonding, melt bonding or pressure bonding. Irrespective of the means of construction, the frame should have an adhesive or tacky material along the second portion thereof to provide preferably releasable attachment to a wearer's face.

In a preferred embodiment of the invention, the frame material comprises a hypoallergenic material such as 3M Corporation's Medical Specialties Health care division's product number 1526 provides release from the wearers face with little or no discomfort. According to 3M product testing, the 1526 material exhibits the following material properties:

(1) Adhesion to steel: Minimum 850 g/25 mm 30 oz/in (8.33 N125 mm)
(2) Liner release: Maximum 50 g (0.49 N)/25 mm
(3) Tape caliper w/o liner 5.0 mils–1.0 mil
(4) Product as specified above in 1–3 as supplied in original packaging, will maintain stated test properties for a period of 2 years, when stored at a temperature between 50–80 degrees F. and a relative humidity between 40–60 percent.

In FIG. 4 is shown again lens 12 and frame 14 which generally make up the novel eyewear of the present invention. Frame 14 overlays lens 12 where adhesive side of the frame 14 is attached or secured to lens 12 at first portion 30 and partially exposed at second portion 32 to secure to a user's face. Frame 14 generally runs along perimeter 18 of lens 12. In addition to providing adhesive means for preferably releasable attachment to a user's face, second portion 32 provides for releasable attachment to a backing layer prior to usage by a user. During assembly of the eyewear 10, and also afterwards during storage, second portion 32 of frame 14 provides releasable attachment to a material such as a backing layer.

Figure 4:
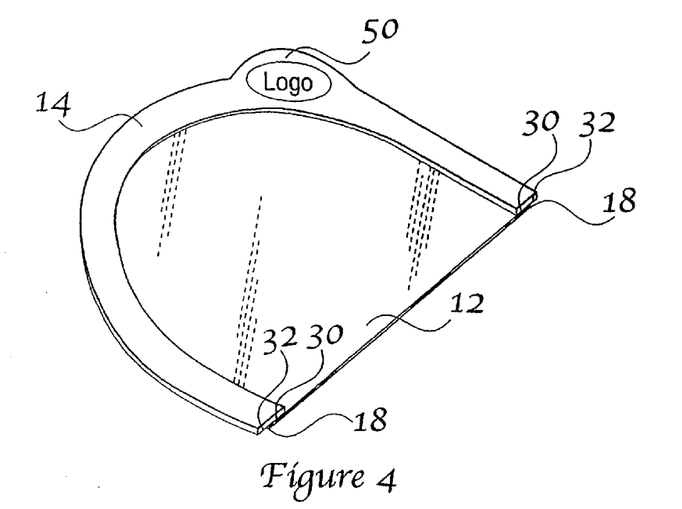
FIG. 4 is a perspective view of eyewear according to the present invention in cross section.

Tab 50 is an appendage upon which can be placed a logo or other identifying indicia. Tab 50 provides more importantly a portion of frame 40 from which a user can grasp to remove the eyewear assembly from the backing layer used during storage or from the user's face once the user is done using the eyewear and wants to dispose of the eyewear. Thus, tab 50 provides for easy removal from backing paper and for placement of insignia or logo.

Figure 5:
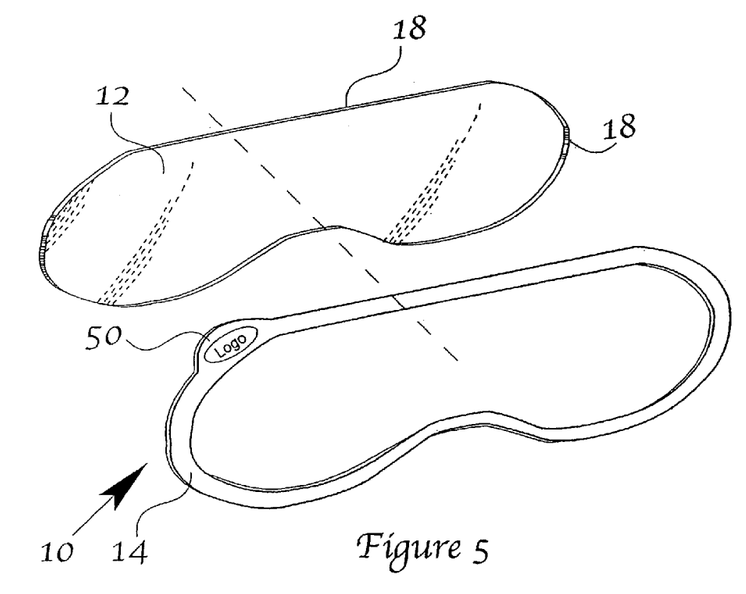
FIG. 5 is an exploded view of eyewear according to the present invention

FIG. 5 generally shows the construction of eyewear 10. Eyewear 10 generally comprises a two-piece construction comprising lens 12 and frame 14, where lens 14 overlays lens 12 generally along the perimeter 18 of lens 12. As described previously, a first portion 30 provides substantially airtight or watertight seal to lens 12 and second portion 32 extends beyond perimeter 18 of lens 12.

Figure 6:
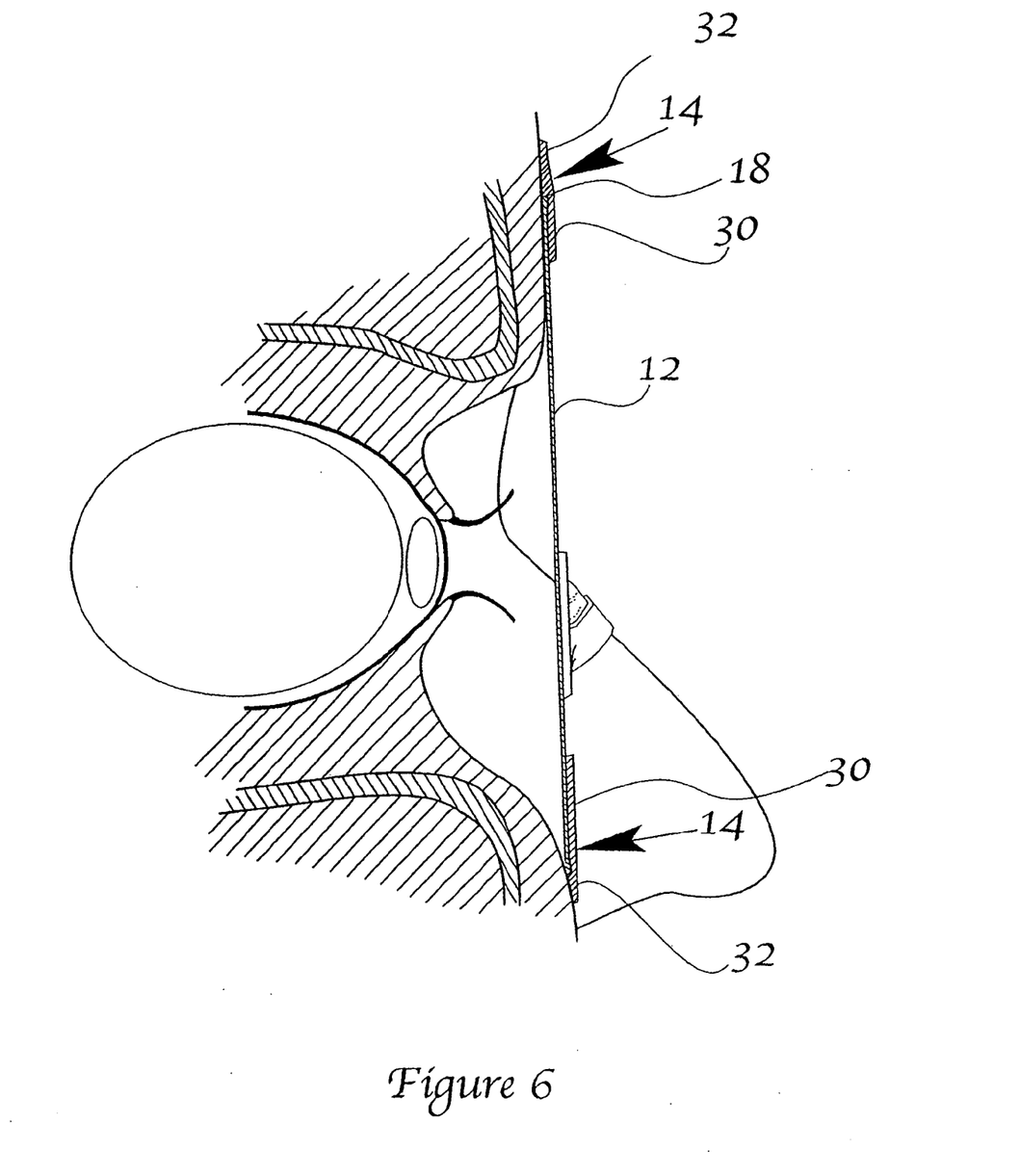
FIG. 6 is a pictorial cross section of eyewear according to the present invention as worn by a user.

FIG. 6 shows the eyewear 10 in use. Lens 12 covers a wearer's eye. Frame 14 comprising first portion 30 and second portion 32 runs along perimeter 18 of lens 12.

First portion 30 provides suitable attachment to lens 12 while second portion 32 extend beyond perimeter 18 and preferably beyond any facial hair of the wearer such as the eyebrows to secure to wearer's skin in a releasable fashion. FIG. 6 also illustrates how frame 12 follows the contours of the wearer's face particularly along the bridge of the nose.

Figure 7:
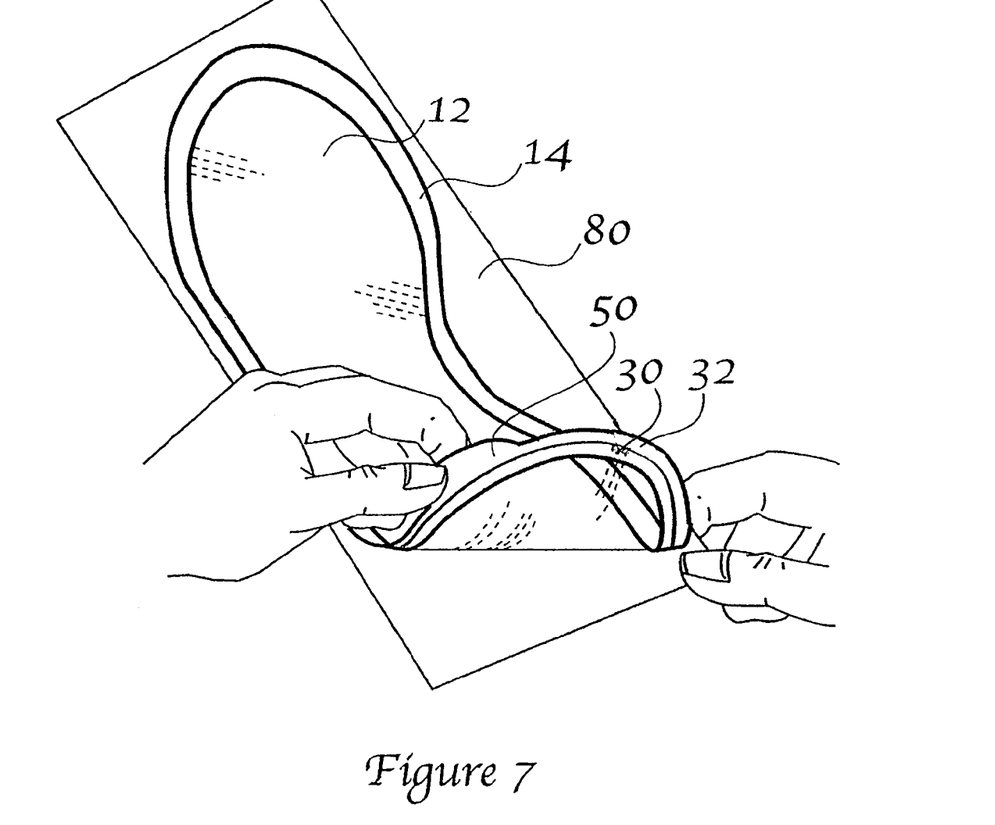
FIG. 7 is an illustrative view of eyewear according to the present invention as partially packaged with a backing layer.

FIG. 7 generally illustrates how the eyewear 10 could be packaged for use by a wearer. The eyewear assembly comprising lens 12 and frame 14 can be positioned on a backing layer 80 during storage and transport whereby second portion 32 provides releasable attachment to backing 80. Tab 50 provides an appendage from which a wearer can remove eyewear 10 from backing 80.

Backing 80 can be any suitable material that is complimentary to adhesive side 16 of frame 14 to provide releasable attachment of the eyewear to backing 80. Polyethylene coated, bleached Kraft paper liner, preferably with a basis weight of 63 pounds, silicone coated one side, which has a nominal caliper of 4.9 mil is a suitable material.

The user, after opening the packaging (not shown), removes the assembled eyewear 10 and applies it directly to their face, covering their eyes.

Figure 8:
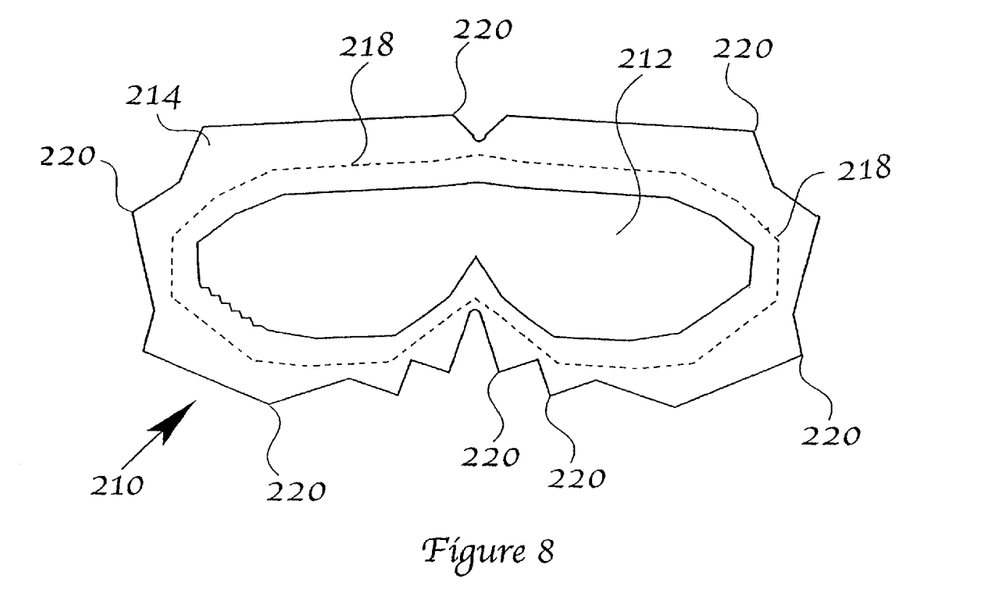
FIG. 8 is a top plan view of an alternative embodiment of eyewear according to the present invention.

FIG. 8 illustrates an alternative embodiment of the novel eyewear. Eyewear 210 comprises lens 212 and frame 214 having a perimeter 218. Frame 214 have a plurality of notches 220 that provide better arrangement of eyewear around the contours of a user's face. The geometry of the frame 214 allows for easier manufacturing of the eyewear 210. For ease of manufacture, eyewear 210 is made of generally flat materials. The generally flat assembly in order to more readily conform to the user's facial structure incorporates a plurality of notches 220 to aid in conforming to the contours of a wearer's face. For example, as the frame 214 and lens 212 conforms to the contours of a wearer's face around the nose of the wearer, the tips or points of the facets at the nose area move closer together as they follow the projected curvature of the nose. Without the facets, lens 214 would buckle, folding onto itself, creating the potential for leaks as well as increasing drag against water in competitive swimming events. Just as in previous embodiments, frame 214 runs along perimeter 218 of lens 212.

Figure 9:
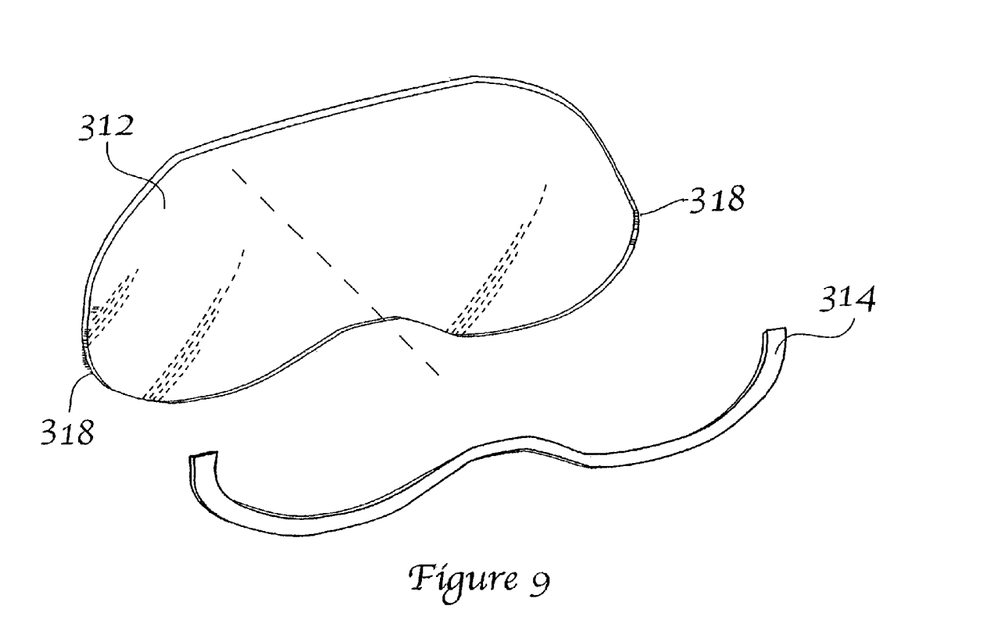
FIG. 9 an exploded view of an alternative embodiment of eyewear according to the present invention.

FIG. 9 illustrates an alternative embodiment of the novel eyewear. This alternative embodiment could be useful for medical application as a protective splash shield from bodily fluids. The lens 312 is oversized and extends horizontally to the user's temple and vertically, well above the brow line. The frame 314 runs along a lower half of the perimeter 318 of lens 312, leaving the upper half of this eyewear embodiment open to the environment. The frame has first and second portions that adhere, respectively, to the lens along the perimeter and the cheek and nose of the user on a lower half of the eyewear. This allows for free air movement between the lens 312 and the user's face along the top portion of the alternative embodiment The free exchange of air ensures that no fog will form on the inside of the lens 312 to ensure maximum visibility for the health care worker.

Figure 10:
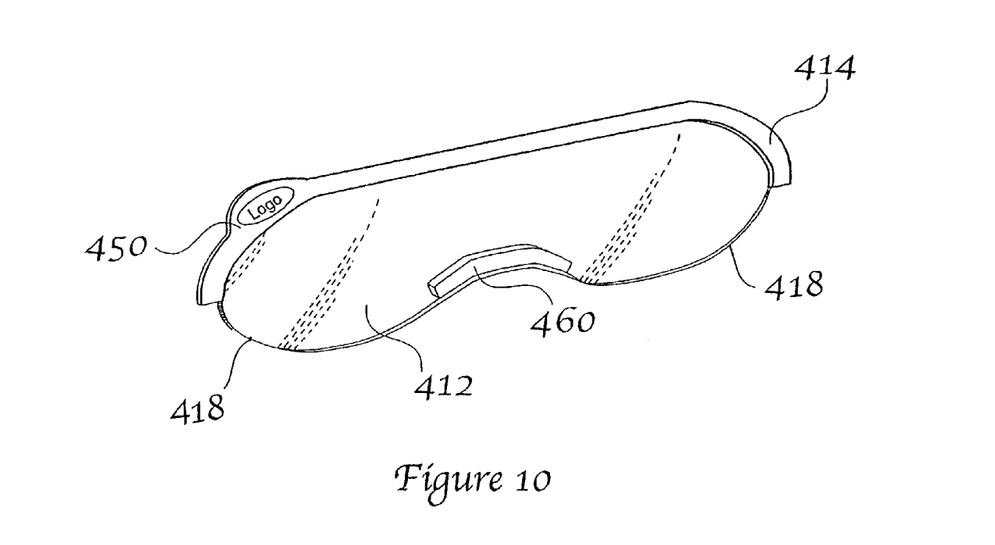
FIG. 10 is a perspective view of an alternative embodiment of eyewear according to the present invention.

FIG. 10 illustrates another alternative embodiment of the novel eyewear. In this alternative embodiment the eyewear includes lens 412 and frame 414 and further comprises nose pad 460. Frame 414 runs along perimeter 418 of lens 412 in an upper half of same. Nose pad 460 is a material comprising a ¼ in. thick, high grade, non-toxic, non-skin irritating, vinyl foam material such as Gaska Tape, Inc.'s product MC2010-NA, which provides a cushioned support of the lens 412 on the wearer's face adjacent the bridge of the nose. In a preferred embodiment of the alternative invention, the lens 412 material comprises a 5 mil polyester film, such as Dupont's Mylar brand product with UV protective properties and tinting for glare reduction.

Partial frame 414 adheres to the temple and brow line of the user allowing for free air movement between the lens 412 and the user's face along the lower portion of the alternative embodiment. The free exchange of air ensures that no fog will form on the inside of the lens 412 to ensure maximum visibility for the user. The seal created along the brow line by the partial frame 414 also ensures that during activity as the user sweats the sweat will be shielded from the eyes and it cannot pass between the frame 414, the lens 412 and the user. Frame 412 includes a tab 450.

In the case of infants and smaller children or during aggressive sports, the adhesive properties of the frame ensures that the eyewear stays in place and provide consistent UV protection, where traditional glasses can easily fall off during activity. In a medical application for treatment of jaundice in infants using UV light to reduce bilirubin amounts where the lens is opaque to protect the eyes from the sun lamp used to cure such condition.

Manufacturing Process

Materials

Sealing frame material is preferably a medical grade, plastic, conformable adhesive tape that is coated with a hypoallergenic, pressure sensitive adhesive. Exposed, non-adhesive side is capable of accepting printing for graphic and text treatments. The adhesive is applied during tape manufacture by the tape maker, such as 3M Corporation. In a preferred embodiment of the invention, frame material comprises a hypoallergenic material such as 3M Corporation's Medical Specialties Health care division's product number 1526, being a 3.6 mil thick, transparent, polyethylene film, coated on one side with a hypoallergenic pressure sensitive acrylate adhesive. The tape is supplied on a polyethylene coated, bleached Kraft paper liner, with a basis weight of 63 pounds, silicone coated one side, which has a nominal caliper of 4.9 mil. According to 3M product clinical data summaries for safety testing, the 1526 material has been subjected to suitable safety tests.

Lens material is preferably a plastic, semi-rigid, conformable, transparent material that can be clear or tinted. Lens material can be treated so that the interior will resist fogging as well as the exterior treated to reduce or eliminate the passage of ultraviolet light The assembled sealing frame and lens is mounted to a release backing 80, which is removed and disposed of by the wearer prior to placement on their face. The tape is supplied on a polyethylene coated, bleached Kraft paper liner, with a basis weight of 63 pounds, silicone coated one side, which has a nominal caliper of 4.9 mil.

The entire assembly is enclosed within a thin, waxed paper package (not shown) to protect the product during shipment.

Production Process

The sealing frame and lens materials can be cut to net shape using a CNC knife plotter or using a die cutting process, (hereinafter referred to generically as a cutting machine). In either case, the base material is supplied in rolls with pin-fed registration holes along each edge lengthways. The material is fed into the cutting machine at a controlled rate where multiple segments are cut progressively or simultaneously. Once cut the web or waste material is removed and disposed of or recycled. The lens and sealing frame components are assembled by placing the lens onto the sealing frame such that the adhesive on the sealing frame overlaps onto the lens border causing a bond between the materials; however, as described previously, the frame material extends laterally beyond the edge of the lens material to provide adhesive means for preferably releasable attachment to the wearer's face. Once assembled a release backing is applied, the finished assembly is then packaged for individual sale.

Construction means via converting the base materials, which are supplied in rolls are as follows. First slitting the base materials into nominal widths providing ample area to nest the finished shaped parts within. Net shape of the finished parts is achieved through automated rotary or steel rule die cutting operations where the lens is cut free from the base material web and the frame is kiss cut where the web is removed from the Kraft backing leaving the frame on the backing. Lens and frame are roll joined, printed, packaged and cut down into individual packages.

The invention claimed is:

1. Eyewear comprising:
   a lens adapted to cover at least one of a user's eyes, the lens comprising a sealed perimeter portion and an unsealed perimeter portion; and
   a sealing frame having an adhesive side, the adhesive side comprising:
      a first adhesive portion forming a seal between the frame and the sealed perimeter portion of lens; and
      a second adhesive portion forming a seal between the frame and a user's face, and wherein, when adhered to a user's face, the unsealed perimeter portion is open to environment, allowing free air movement between the lens and a user's face at the unsealed perimeter portion.

2. The eyewear of claim 1 wherein the second adhesive portion provides a means for forming a substantially airtight and water tight seal between the frame and at least a portion of the user's face adjacent the perimeter of the lens.

3. The eyewear of claim 1, wherein the frame has an adhesive on a side opposite the exposed side of the frame disposed between the frame and, in one portion, the face of the user and, in a second portion, between the frame and the lens.

4. The eyewear of claim 1, wherein the sealed perimeter portion comprises an upper edge.

5. The eyewear of claim 1, wherein the sealed perimeter portion comprises a lower edge.

6. The eyewear of claim 1, wherein the second adhesive portion comprises a flexible material adapted to substantially conform to at least a portion of a user's face, and wherein the adhesive side of the second portion comprises an adhesive material.

7. The eyewear of claim 1, wherein the lens comprises a flexible, transparent thermoplastic material.

8. The eyewear of claim 1, wherein the lens comprises:
   at least one of a semi-rigid transparent material and a rigid transparent material; and
   a contour that substantially conforms to at least a portion of a user's face.

9. The eyewear of claim 1, wherein at least a portion of the lens is coated with at least one of an anti-fogging coating, a UV protection coating, and a water-shedding coating.

10. The eyewear of claim 1, wherein the frame defines at least one notch.

11. Eyewear comprising:
    a) a lens adapted to cover at least one of a user's eyes, the lens comprising a sealed perimeter portion and an unsealed perimeter portion; and
    b) a sealing frame comprising:
       a compliant and resiliently deformable material suitable to conform to a user's face,
          wherein the frame has an adhesive side for sealing the frame to a user's face and, the sealed perimeter portion, and
          wherein, when adhered to a user's face, the unsealed perimeter portion is open to environment, allowing free air movement between lens and a user's face at the unsealed perimeter portion.

12. The eyewear of claim 11, wherein the sealed perimeter portion comprises an upper edge.

13. The eyewear of claim 11, wherein the sealed perimeter portion comprises a lower edge.

14. The eyewear of claim 11, wherein the second adhesive portion comprises a flexible material adapted to substantially conform to at least a portion of a user's face, and wherein the adhesive side of the second portion comprises an adhesive material.

15. The eyewear of claim 11, wherein the lens comprises a flexible, transparent thermoplastic material.

16. The eyewear of claim 11, wherein the lens comprises:
    at least one of a semi-rigid transparent material and a rigid transparent material; and
    a contour that substantially conforms to at least a portion of a user's face.

17. The eyewear of claim 11, wherein at least a portion of the lens is coated with at least one of an anti-fogging coating, a UV protection coating, and a water-shedding coating.

18. The eyewear of claim 11, wherein the frame defines at least one notch.

* * * * *